(12) United States Patent
Behnke, II et al.

(10) Patent No.: US 9,113,887 B2
(45) Date of Patent: Aug. 25, 2015

(54) ELECTROSURGICAL GENERATOR

(75) Inventors: Robert J. Behnke, II, Erie, CO (US);
Donald W. Heckel, Thornton, CO (US);
Robert B. Smith, Loveland, CO (US);
James E. Krapohl, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 558 days.

(21) Appl. No.: 13/443,330

(22) Filed: Apr. 10, 2012

(65) Prior Publication Data

US 2013/0267945 A1    Oct. 10, 2013

(51) Int. Cl.
| | | |
|---|---|---|
| *A61B 18/04* | (2006.01) | |
| *A61B 18/12* | (2006.01) | |
| *A61B 18/14* | (2006.01) | |
| *A61B 18/00* | (2006.01) | |

(52) U.S. Cl.
CPC ......... *A61B 18/1206* (2013.01); *A61B 18/1445* (2013.01); *A61B 2018/0063* (2013.01); *A61B 2018/0072* (2013.01); *A61B 2018/00577* (2013.01); *A61B 2018/00601* (2013.01); *A61B 2018/00648* (2013.01); *A61B 2018/00702* (2013.01); *A61B 2018/00827* (2013.01); *A61B 2018/00875* (2013.01); *A61B 2018/00892* (2013.01)

(58) Field of Classification Search
CPC .......... A61N 1/00; A61B 18/00; A61B 18/02; A61B 18/04; A61B 18/06; A61B 18/08; A61B 18/10; A61B 18/12; A61B 18/14; A61B 18/16; A61B 18/18; A61B 5/05; A61B 5/053

USPC .................................... 606/34; 607/7, 11, 30
See application file for complete search history.

(56) References Cited

U.S. PATENT DOCUMENTS

| | | | |
|---|---|---|---|
| 6,996,487 B2 | 2/2006 | Jutras et al. | |
| 7,300,435 B2 | 11/2007 | Wham et al. | |
| 7,901,400 B2 | 3/2011 | Wham et al. | |
| 2009/0163930 A1 | 6/2009 | Aoude et al. | |
| 2010/0121318 A1 | 5/2010 | Hancock et al. | |
| 2013/0079763 A1* | 3/2013 | Heckel et al. | 606/33 |

* cited by examiner

*Primary Examiner* — Christopher D Koharski
*Assistant Examiner* — Elizabeth K So (57) ABSTRACT

An electrosurgical system for performing an electrosurgical procedure is provided and includes an electrosurgical generator and a calibration computer system. The electrosurgical generator includes one or more processors and a measurement module including one or more log amps that are in operative communication with the processor. The calibration computer system configured to couple to a measurement device and is configured to measure parameters of an output signal generated by the electrosurgical generator. The calibration computer system is configured to compile the measured parameters into one or more data look-up tables and couple to the electrosurgical generator for transferring the data look-up table(s) to memory of the electrosurgical generator. The microprocessor is configured to receive an output from the log amp(s) and access the data look-up table(s) from memory to execute one or more control algorithms for controlling an output of the electrosurgical generator.

12 Claims, 5 Drawing Sheets

| Impedance | Actual Irms | V1Raw | I1Raw | Calculated Vrms | Log V1 | V1 Gain |
|---|---|---|---|---|---|---|
| 100 | 0 | 0.3735 | 0.4622 | 0 | | |
| 100 | 0.03 | 1.6479 | 0.9229 | 3 | 0.021 | 139.88 |
| 100 | 0.073 | 1.9614 | 1.3008 | 7.3 | 0.054 | 134.96 |
| 100 | 0.171 | 2.2368 | 1.5974 | 17.1 | 0.122 | 140.27 |
| 100 | 0.27 | 2.4031 | 1.7644 | 27 | 0.199 | 135.59 |
| 100 | 0.37 | 2.5188 | 1.8728 | 37 | 0.280 | 132.06 |
| 100 | 0.47 | 2.5994 | 1.9534 | 47 | 0.355 | 132.25 |
| 100 | 0.568 | 2.658 | 2.0171 | 56.8 | 0.422 | 134.45 |
| 100 | 0.698 | 2.718 | 2.083 | 69.8 | 0.504 | 138.41 |
| 100 | 0.796 | 2.7612 | 2.1255 | 79.6 | 0.573 | 138.95 |
| 100 | 0.893 | 2.7979 | 2.1687 | 89.3 | 0.638 | 139.88 |

Fig. 6

ELECTROSURGICAL GENERATOR

BACKGROUND

1. Technical Field

The present disclosure relates to an electrosurgical generator. More particularly, the present disclosure relates to electrosurgical generators having a gain calibrated RF logarithmic amplifier sensor.

2. Description of Related Art

RF generators configured for use with electrosurgical instruments are known in the art. In certain instances, one or more logarithmic amplifier, sometimes referred to as "log amps," may be incorporated into the circuitry of the RF generators to compress a large dynamic input range to a more manageable output for a digital signal processor of the RF generator. For example, a typical log amp can have an input range that varies by 10,000 times, e.g., from about 100 µV to about 1V. Conversely, a log amp output, typically, varies by 3 times, e.g., from about 1V to about 3V. To accomplish these log amp input and output ratios, log amps typically have a very high gain bandwidth, which is fairly constant. Due to internal construction of the log amps, however, the log amps have non-linear gain dependency at their inputs, which, in turn, results in decreased accuracy of log amp sensors associated with the log amps.

SUMMARY

In view of the foregoing, there exists a need for RF generators having one or more gain calibrated log amp sensors configured to compensate for gain variance at the input of the log amp.

Aspects of the present disclosure are described in detail with reference to the drawing wherein like reference numerals identify similar or identical elements. As used herein, the term "distal" refers to the portion that is being described which is further from a user, while the term "proximal" refers to the portion that is being described which is closer to a user.

An aspect of the present disclosure provides an electrosurgical system for performing an electrosurgical procedure. The electrosurgical system including an electrosurgical generator that includes at least one processor and a measurement module including at least one log amp in operative communication with the processor. A calibration computer system is configured to couple to a measurement device and is configured to measure parameters of an output signal generated by the electrosurgical generator. The calibration computer system is configured to compile the measured parameters into at least one data look-up table, and couple to the electrosurgical generator for transferring the at least one data look-up table to memory of the electrosurgical generator. The microprocessor is configured to receive an output from the at least one log amp and access the at least one data look-up table from memory to execute at least one control algorithm for controlling an output of the electrosurgical generator.

The at least one log amp may be configured to receive an output from a sensor that is configured to sense an output of the electrosurgical generator.

The measurement device may be a device that measures RMS current. In this instance, the measurement device may include a current toroid that is configured to measure an output current of the electrosurgical device.

The output from the at least one log amp may be a voltage output.

The parameters contained in the data look-up table may include gain of the at least one log amp, output voltage of the at least one log amp, input voltage of the at least one log amp, output current of the electrosurgical generator and output voltage of the electrosurgical generator.

The at least one control algorithm may be configured to calculate a slope and gain of the log amp. The slope and gain of the log amp may be calculated through a dynamic operating range of the log amp. The log amp may be configured to allow a user to vary a slope thereof to obtain an optimum slope through the dynamic operating range.

The control algorithm may utilize a piece-wise linear fit of the gain relative to the measured output of the log amp to correct gain variations of the log amp. Moreover, the control algorithm may utilize an averaging technique of the gain relative to the measured output of the log amp to correct gain variations of the log amp. Further, the control algorithm may utilize a polynomial curve fitting technique of the gain relative to the measured output of the voltage log amp to correct the variations in gain.

The measurement module may include a voltage and current sensor that are configured to measure respective voltage and current on a patient side of an output transformer of the measurement module. The voltage and current sensors may be isolated from a patient and referenced to ground of the electrosurgical generator by isolating and/or reducing a voltage sense line with the use of one or more capacitors.

An aspect of the instant disclosure provides a computer calibration system for calibrating measurement circuitry of an electrosurgical device. The computer calibration system includes a measurement device that is configured to measure an output of the electrosurgical device. A memory that stores measurement data includes a plurality of current and voltage values of at least one log amp of the measurement circuitry, a plurality of gain values of the log amp, a plurality of current and voltage values of the electrosurgical device and a plurality of impedance values of a load coupled to the electrosurgical device. A processor may be configured to execute one or more control algorithms to compile the measurement data into at least one data look-up table. A communication interface may be configured for transferring the at least one data look-up table to memory of the electrosurgical device when the computer calibration system is coupled to the electrosurgical generator.

The at least one log amp may be configured to receive an output from a sensor that is configured to sense an output of the electrosurgical device.

The measurement device may be configured to measure RMS current. In this instance, the measurement device may include a current toroid that is configured to measure an output current of the electrosurgical device.

An aspect of the instant disclosure provides a method for calibrating measurement circuitry of an electrosurgical device. An output of the electrosurgical device is measured. An output of at least one log amp of the measurement circuitry of the electrosurgical device is measured. A data look-up table including measurement data obtained from the measuring steps is compiled. A slope and gain of the at least one log amp is calculated based on the measurement data obtained from the measuring step. At least one control algorithm utilizing the calculated slope and gain is executed. A gain of the log amp based on an output of the log amp to calibrate the measurement circuitry is recalculated.

The at least one control algorithm may utilize a piece-wise linear fit of the gain relative to the measured output of the log amp to correct gain variations of the log amp. Moreover, the at least one control algorithm may utilize either an averaging technique or a polynomial curve fitting technique of the log amp gain relative to the measured output of the voltage log amp to correct the variations in gain.

BRIEF DESCRIPTION OF THE DRAWINGS

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
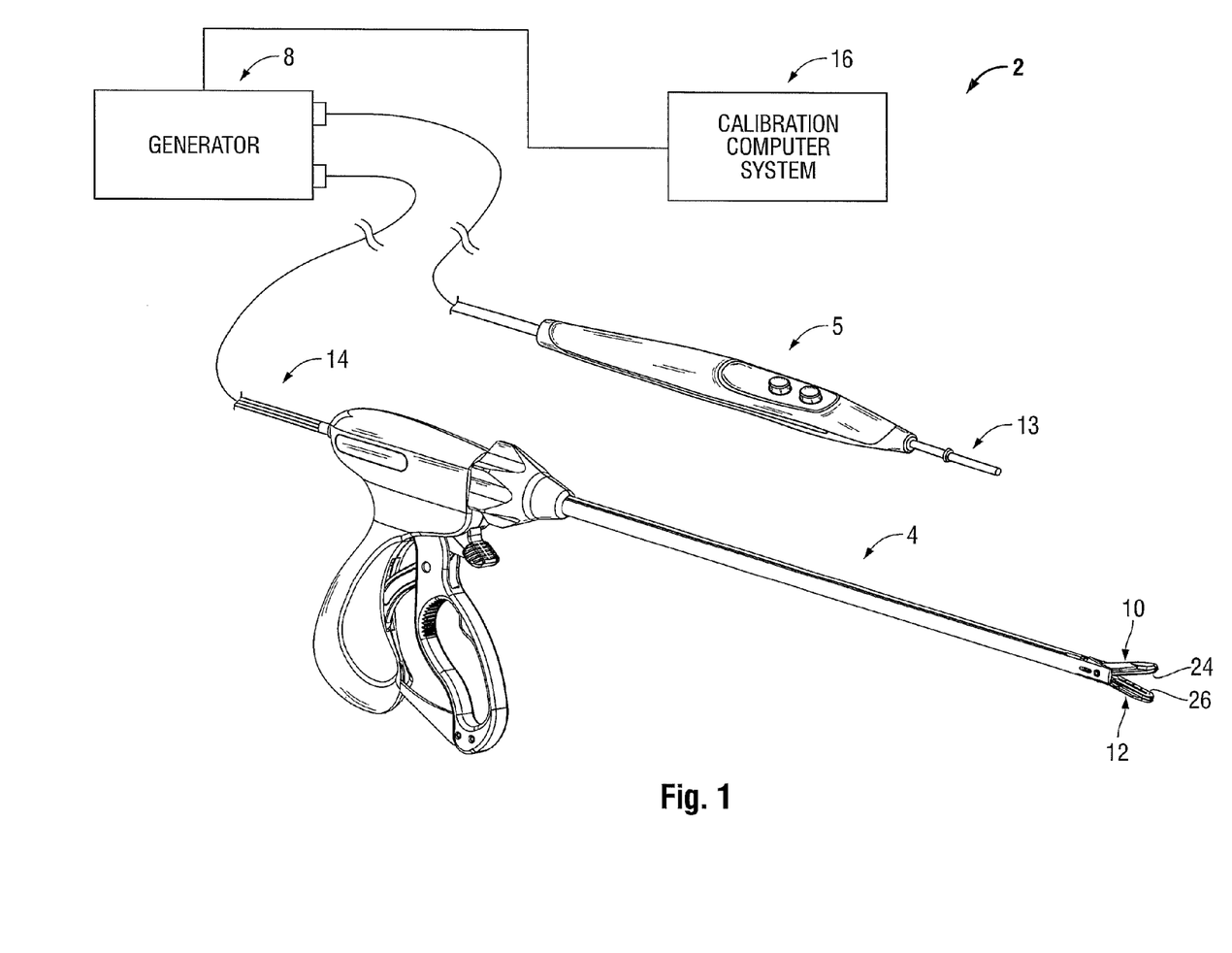
FIG. 1 is a perspective view of an electrosurgical system including a generator, calibration computer system, and electrosurgical instrument(s) according to an embodiment of the present disclosure.

FIG. 1 is a perspective view of an electrosurgical system 2 that includes a calibration system 16 according to embodiments of the present disclosure. System 2 includes an electrosurgical generator 8 including electronic circuitry that generates radio frequency power for various electrosurgical procedures (e.g., sealing, cutting, coagulating, or ablating). The electrosurgical generator 8 may include a plurality of connectors to accommodate various types of electrosurgical instruments, e.g., a forceps 4, pencil 5, etc., that are configured to deliver the electrosurgical energy to tissue during a surgical procedure. In the illustrated embodiment, each of the forceps 4 and pencil 5 includes one or more electrodes that are configured to provide electrosurgical energy to treat tissue. For example, forceps 4 may be configured as a bipolar electrosurgical forceps including jaw members 10 and 12 (FIG. 1) having a respective electrode 24, 26 (FIGS. 1 and 2) that are each connectable to the electrosurgical generator 8 via a cable 14 (FIG. 1). Alternately, the forceps 4 may be a monopolar electrosurgical forceps, in which case one of the jaw members 10 and 12 includes an active electrode, and a return electrode is operably supported on a return pad (not shown) that is configured to contact a patient. In the illustrated embodiment, pencil 5 includes an active electrode 13, and a return electrode is operably supported on a return pad (not shown) that is configured to contact a patient. For the remainder of the discussion, electrosurgical system 2 and calibration system 16 are described in terms of use with a bipolar electrosurgical forceps 4.

Figure 2:
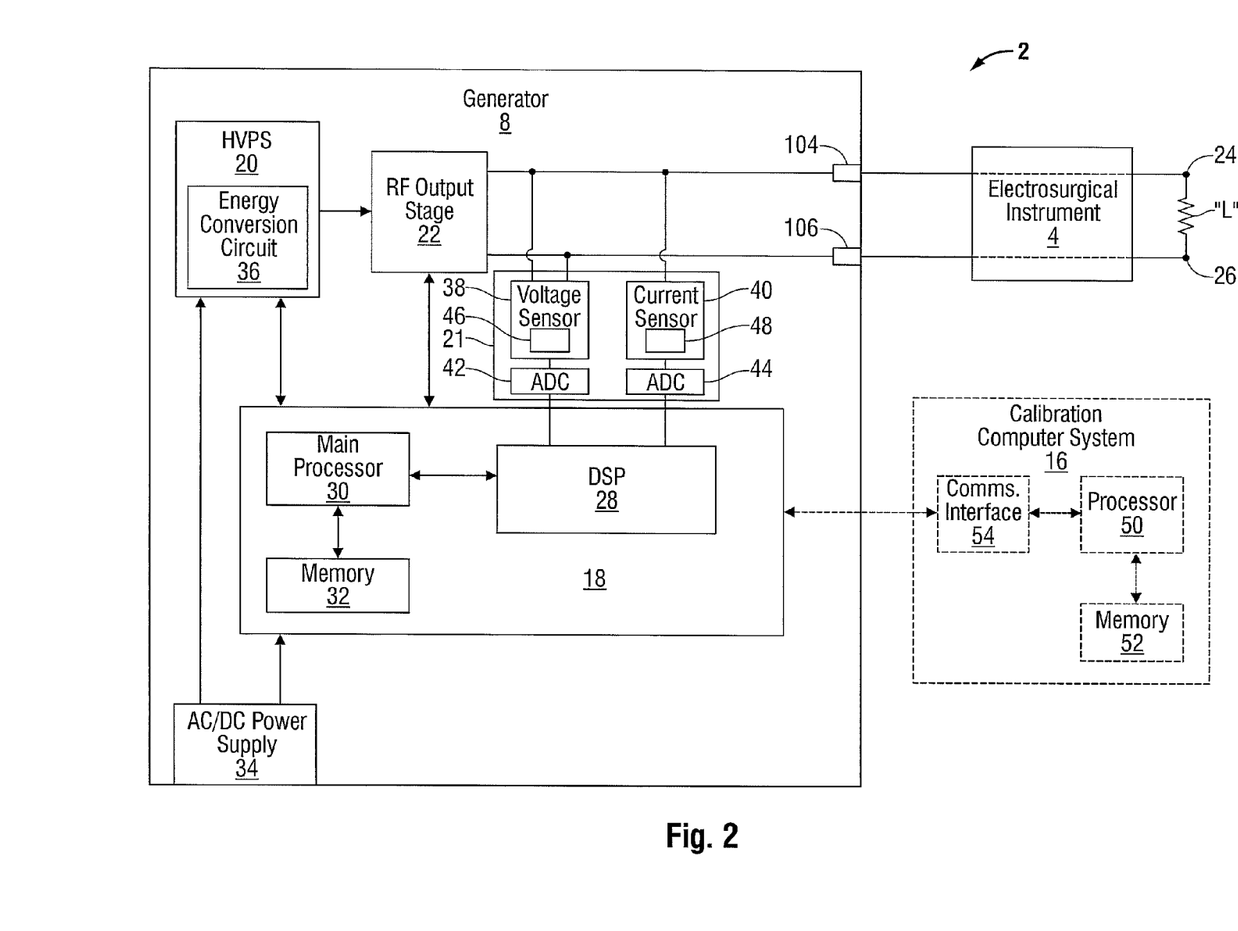
FIG. 2 is a block diagram of the electrosurgical system depicted in FIG. 1.

FIG. 2 is a block diagram of an electrosurgical system 2, which includes the generator 8, forceps 4 and calibration computer system 16 of FIG. 1. Briefly, generator 8 includes a controller 18, a high voltage power supply 20, and a radio frequency output stage 22, which operate together to generate an electrosurgical signal to be applied to tissue through electrodes 24, 26 of forceps 4. Controller 18 includes a digital signal processor (DSP) 28, a main processor 30, and a memory 32. The controller 18 may be any suitable microcontroller, microprocessor, PLD, PLA, or other digital logic device. Memory 32 may be volatile, non-volatile, solid state, magnetic, or other suitable storage memory.

The controller 18 may also include various circuitry that serves as an interface between the main processor 30 and other circuitry within the electrosurgical generator 8 (e.g., amplifiers and buffers). The controller 18 receives various feedback signals that are used by the main processor 30 and/or the DSP 28 to generate control signals to control various subsystems of the generator 8, including the HVPS 20 and the RF output stage 22. These subsystems are controlled to generate electrosurgical energy having desired characteristics for performing surgical procedures on tissue, which is represented in FIG. 2 by a test load "L."

The generator 8 includes an AC/DC power supply 34 that receives power from an alternating current (AC) line source (not explicitly shown) and converts the AC line power into direct current (DC), and, in turn, provides the DC power to an energy conversion circuit 36. The energy conversion circuit 36 then converts the DC power at a first energy level into DC power at a second, different energy level based upon control signals received from the controller 18. The energy conversion circuit 36 supplies the DC power at the second, different energy level to the RF output stage 22. The RF output stage 22 converts the DC power into a high-frequency alternating current (e.g., RF), which may then be applied to tissue.

Figure 3:
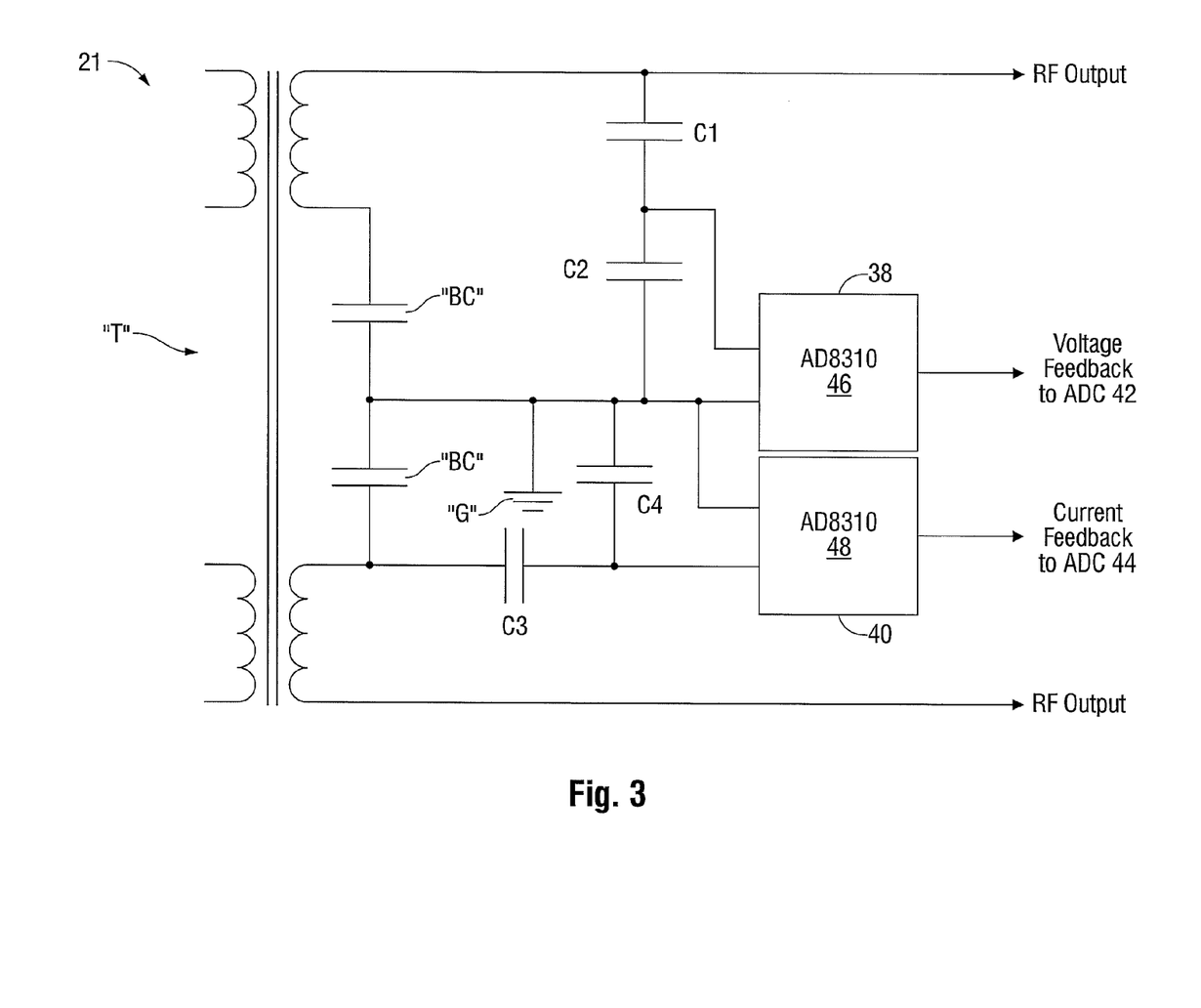
FIG. 3 is a schematic diagram of an RF output stage of the generator depicted in FIGS. 1 and 2.

In accordance with the instant disclosure, the electrosurgical generator 8 includes a measurement module 21 (FIGS. 2 and 3) that is configured to determine voltage, current, impedance, and power at a tissue site so that the controller 18 can use these measurements to control the characteristics of the electrosurgical output. The measurement module 21 includes a voltage sensor 38 and a current sensor 40 coupled to the output of the RF output stage 22 (FIG. 2). The voltage sensor 38 senses the voltage across the output of the RF output stage 22 and provides, via a log amp 46, an analog signal representing the sensed voltage to an analog-to-digital converter (ADC) 42, which converts the analog signal representing voltage into digital form (FIGS. 2 and 3). Similarly, the current sensor 40 senses the current at the output of the RF output stage 22 and provides, via a log amp 48, an analog signal representing the sensed current to another ADC 44, which converts the analog signal representing current into digital form (FIGS. 2 and 3).

The DSP 28 receives the sensed voltage and sensed current data from the respective log amps 46 and 48 and uses it to calculate the impedance and/or the power at the tissue site. The main processor 30 of the controller 18 executes algorithms that use the sensed voltage, the sensed current, the impedance, and/or the power to control the HVPS 20 and/or the RF Output Stage 22. For example, the main processor 30 may execute a PID control algorithm based upon the calculated power and a desired power level, which may be selected by a user, to determine the amount of electrical current that should be supplied by the RF output stage 22 to achieve and maintain the desired power level at the tissue site. As discussed in greater detail below, the DSP 28 utilizes one or more control algorithms to calibrate the received sensed voltage and current data to obtain a more accurate representation of the RMS voltage (Vrms) that is transmitted to the forceps 4.

FIG. 3 illustrates a block diagram of internal components of the measurement module 21 including the voltage and current sensors 38 and 40 connected to the RF output stage 22. Voltage and current sensors 38 and 40 are measured on the patient side of an output transformer "T." In the illustrated embodiment, both the voltage and current sensors 38 and 40 are duplicated for redundant sensing (only one of each is shown). The sensors 38, 40 are isolated from the patient and are referenced to ground "G" of the generator 8 (FIG. 3). With respect to the voltage, this is accomplished by isolating and reducing a voltage sense line with the use of a pair of capacitors C1 and C2 (FIG. 3). For the current, a center tap transformer configuration is utilized including a pair of blocking capacitors "BC" between the ground "G" of the generator 8 and transformer "T". The blocking capacitors "BC" are used as a current sensing element instead of a traditional lossy element such as, for example, a resistor. The isolation and signal reduction for the current sense line is maintained using a pair of capacitors C3 and C4 (FIG. 3). The capacitors C1-C4 may be any suitable type of capacitors including without limitations polyphenylene sulphide (PPS) film capacitors, ceramic chip capacitors NPO (COG) and the like. In accordance with the instant disclosure, capacitors C1-C4 are ceramic chip capacitors NPO (COG) and are chosen for their voltage and thermal stability. The aforementioned capacitor configuration facilitates maintaining a consistent overall gain of the measurement module 21 and, in particular log amps 46 and 48.

Log amps 46 and 48 may be any suitable type of log amp. A suitable log amp may be an AD8310 manufactured by Analog Devices (FIG. 3). This particular log amp was chosen because of its low current draw (e.g., approximately 8 mA), small footprint (e.g., approximately 4×5 mm), a suitable differential AC input that ranges from about −91 dBV to about 9 dBV, a suitable DC level output that ranges from about 0.4V to about 2.6V, and a large dynamic range that ranges from about −91 dB to about 4 dB. The AD8310 log amp utilizes minimal external components as compared to other log amps that are sometimes utilized in conventional generators. Other suitable log amps that may be utilized in accordance with the present disclosure include: AD8307, AD8318, AD8317, ADL5513, AD8363 (RMS) all manufactured by Analog Devices, HMC612LP manufactured by Hittite, LTC5507 manufactured by Linear Technology, and TL441 manufactured by Texas Instruments.

Figure 4:
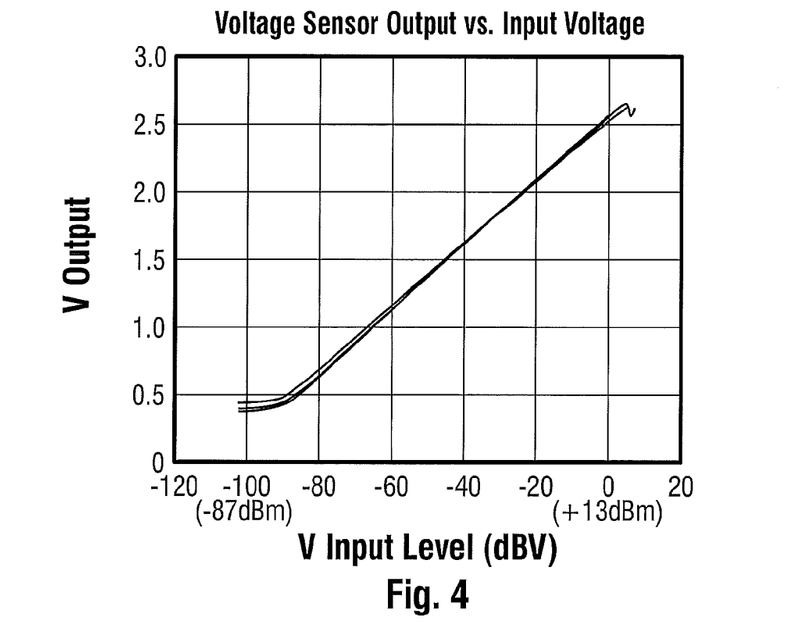
FIG. 4 is graphical illustration of an output voltage of a log amp plotted against an input voltage of the log amp across the dynamic range of the log amp.

FIG. 4 shows a typical performance characteristic of an output of the log amp 46. In accordance with the instant disclosure, a slope is used to derive a linear slope equation in the form of y=mx+b, where m is the slope of the output of the log amp 46 and b is the intercept of the log amp 46 at a 0 dBV input. The X axis shows the input in dBV and the Y axis shows the corresponding output of the log amp 46. Log amp 46 includes a slope input (not explicitly shown) that gives the flexibility to increase the slope of the thereof. In accordance with the instant disclosure, to balance between input versus output range, the slope was increased to 40 mV/dB; this was done by adding a 23.2 KΩ resistor between two or more pins of the log amp 46. With the increased slope of 40 mv/dB the output of the log amp 46 is 1.2V and an intercept point of the log amp 46 is 2.95 at the 0 dBV point, see FIG. 4. The equation for the output of the log amp 46 is expressed as:

$$V\text{out}=0.040x+2.95 \qquad (1)$$

where x is the value in dB of the input signal.

Equation (1) can be solved for x in volts (not dB) by rewriting equation (1) with dB:

$$V\text{out}=\text{Slope}*[20*\log(V\text{in})]+2.95 \qquad (2)$$

the slope from equation (1) equals 0.04, Vin equals the input voltage to the log amp 46 and the 20 in equation (2) comes from the conversion of dBV to V which is:

$$dBV=20*\log(V) \qquad (3)$$

solving for Vin:

$$V\text{in}=10^{\wedge}[(V\text{Out}-2.95)/(20*\text{Slope})] \qquad (4)$$

the power of 10 comes from the inverse of the log function.

With reference again to FIG. 3, the voltage signal into log amp 46 is a voltage divider using the ratio of C1 and C2. This voltage signal is equal to:

$$V\_RF=V\_\text{Out}\times(XC_2/(XC_2+XC_1)) \qquad (5)$$

where XC=1/(2πfC), V_Out is the output voltage of the generator 8, f is the operating frequency of the generator 8, and C is the value of the capacitors.

The current signal into the log amp 40 may be derived from measuring the voltage integrated across the blocking capacitors "BC". The voltage across the blocking capacitor "BC" is related to the current through the blocking capacitor "BC" using the equation:

$$dv=I\times dt/C \qquad (6)$$

where I is the output current of the generator 8, C is the value of the blocking capacitor "BC", dv is the change in voltage across the capacitor "BC", and dt is the switching cycle time.

In some embodiments, to reduce noise on the current signal, a differential pair (not explicitly shown) may be run from the blocking capacitors "BC" back to an input of the log amp 48. In particular, a low pass differential filter (with a pole of suitable frequency, e.g., about 100 KHz) may be added in series with the log amp 48. One or more low pass differential filters may also be added in series with the log amp 46 to facilitate reducing noise on the current signal.

The aforementioned configuration of the log amps 46 and 48 and low pass filter facilitates maintaining a consistent overall gain of the measurement module 21.

To accurately control the electrosurgical energy applied to tissue, the controller 18 needs to accurately sense the voltage and current at the tissue. As noted above, however, the voltage sensed by the voltage sensor 38 and the current sensed by the current sensor 40 may be inaccurate because of the internal construction of the log amps 46 and 48. In particular, log amps 46 and 48 may have an internal gain that is dependent on the input voltage such that the gain of the log amps 46 and 48 is not constant across a dynamic range of the log amps 46 and 48. The dynamic range of the log amps 46 and 48 may be measured from a voltage minimum (or current minimum) to a voltage maximum (or current maximum). This gain variation present for both log amps 46 and 48 may result in decreased accuracy of log amp sensors 38 and 40. In other words, the voltage and current measured at the RF output stage 22 by the voltage and current sensors 38, 40 may not equal the actual voltage and current at the load "L" (e.g., tissue) because of the non-linear gain dependency at the inputs of the log amps 46 and 48.

The electrosurgical system 2 is configured to calibrate sensors 38 and 40 to compensate for the gain losses of the log amps 46 and 48 that introduce errors into the sensor data provided by the sensors 38 and 40. In particular, a slope of the log amps 42 and 44 and an overall gain of the measurement module 21 is calculated via the calibration computer system 16. In accordance herewith, the overall gain of the measurement module 21 takes into account the voltages from the capacitor divider network, attenuation due to the filter, and the gain through the log amp 38 and/or 40. For illustrative purposes, the overall gain of the measurement module 21 is obtained using the gain of the log amp 46 that relates to measurements sensed by the voltage sensor 38.

Figure 5:
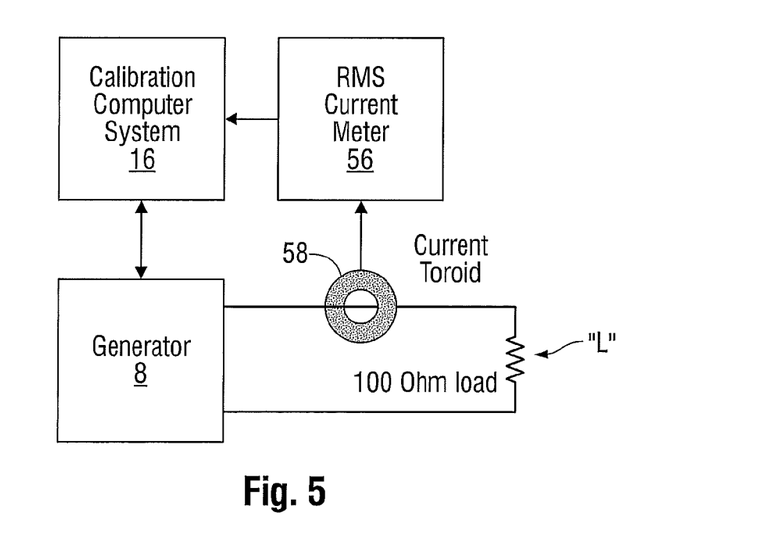
FIG. 5 is a block diagram of the electrosurgical system depicted in FIG. 1 coupled to a measuring device and a test load.

The slope and gain are calculated via calibration computer system 16. Calibration computer system 16 is in connection with the controller 18 of the generator 8 and includes a processor 50, a memory 52, and a communications interface 54. Calibration computer system 16 utilizes one or more suitable measuring devices to measure output voltage and current. In the illustrated embodiment, a RMS meter 56 in communication with a current toroid 58 is utilized to measure output current Irms sent to the test load "L" as shown in FIG. 5. The output voltage Vrms can be obtained by multiplying the output current by the resistance of the test load "L."

In some embodiments, the generator 8 is connected to the calibration computer system 16, RMS meter 56 including the current toroid 58, and a 100 ohm test load "L." In this instance, for example, calibration computer system 16 configures the generator 8 to operate in an open loop mode, sets a target value(s), and turns on the generator 8 until the generator reaches the target value(s). In some embodiments, the power supply duty cycle of the generator 8 is varied to produce an RF output from 4 volts rms to 92 volts rms, e.g., through the dynamic range of the log amps 46 and 48. Calibration computer system 16 records the data measured by the generator 8 and RMS current meter 56, see table (1) in FIG. 6. In embodiments, this data can be loaded into one or more suitable templates, e.g., a formatted Excel template, for analysis of a load curve to plot error.

Figure 6:
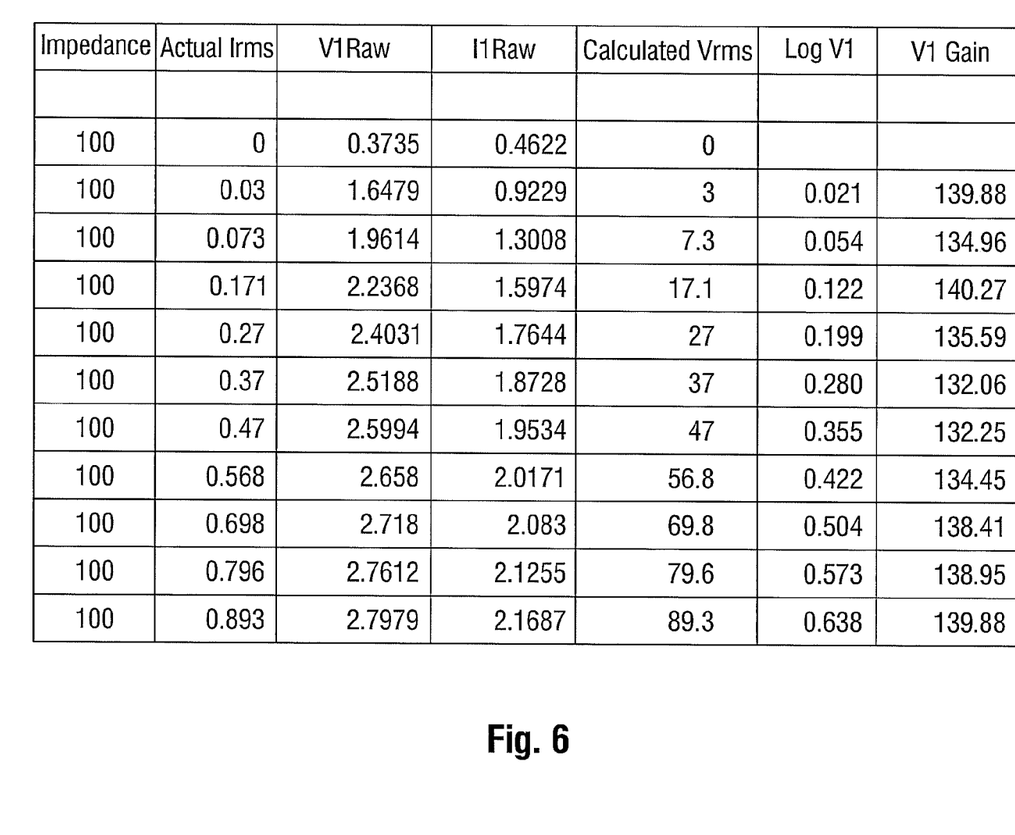
FIG. 6 is a table illustrating tabulated measured and calculated data taken across a dynamic range of a log amp depicted in FIG. 2.

Table (1) in FIG. 6 lists the impedance of the test load "L", e.g., a 100Ω load, measured Irms, V1raw (output voltage of log amp 46), I1raw (output current of log amp 48) and calculated Vrms which is obtained by multiplying a corresponding Irms by the test load "L" impedance (e.g., 0.893 A×100Ω=89.3 V). The processor 50 accesses measurement data of table (1) and stores the measurement data in the memory 32 of the generator 8. This data is accessible by the DSP 28 to execute one or more control algorithms for controlling an output of the generator 8.

In some instances, the slope is calculated by dividing the dynamic range of the output of the voltage log amp 46 over the measured range of the output of the generator 8 in dB using the following equation:

$$\text{Slope} = (\text{Log}_{out\_}\text{max} - \text{Log}_{out\_}\text{min}) / ((20 \times \log(\text{Gen}_{out\_}\text{max})) - (20 \times \log(\text{Gen}_{out\_}\text{min}))) \quad (7)$$

where $\text{Log}_{out\_}$max is the maximum output value of the log amp 38 recorded (2.7979), $\text{Log}_{out\_}$min is the minimum value of the log amp 38 recorded (1.6479, (0.3735 in this column is used to verify the offset of the log amp 46 at no output of the generator 8; this offset should be between 0.3 to 0.5)), $\text{Gen}_{out\_}$max is the max output of the generator 8 (89.3) and $\text{Gen}_{out\_}$min is the min output of the generator 8 (3, (the 0 may be ignored)). It has been found that the slope of the log amp 46 is equal to about 39 mV/dB and is linear over the dynamic range, as shown in FIG. 4, for example.

To measure the gain of the log amp 46 (e.g., overall gain of the measurement module 21), first the output voltage of the log amp 46 is translated to an input voltage, using the following equation:

$$V\text{in} = 10^{\wedge}[(V\text{out} - 2.95)/(20 \times \text{Slope})] \quad (8)$$

where the "slope" is the slope of the voltage log amp 46 and Vout is the Vraw from table (1). The output of the log amp 46 equals 2.7979V at a calculated output voltage Vans from the generator 8 of 89.3V. Placing this into equation (4) and using the 39 mV for the slope, the input voltage is 0.638V, see Log V1 column of table (1) in FIG. 6; this is the actual voltage at the input of the log amp 46. The gain can now be calculated using the equation:

$$\text{Gain}V = \text{Calculated\_}V\text{rms}/V\text{in} \quad (9)$$

in this instance the gain is equal to 139.88 (e.g., 89.3 v/0.638 v). The gain for each measured output voltage Vraw of the log amp 46 and corresponding output voltage Vrms of the generator 8 can be calculated in a similar manner and recorded. As can be appreciated, the more measurements taken through the dynamic range of the log amp 46 the more accurate the calculate gain will be. Multiplying equation (4) with the gain calculated in equation (9) gives an accurate representation of the output of the generator 8 referenced to the output of the log amp 46 when the generator 8 is coupled to a test load, see equation (10) below.

$$\text{Out} = \text{Gain} \times 10^{\wedge}[(V\text{out} - 2.95)/(20 \times \text{Slope})] \quad (10)$$

Equation (10) is stored in memory 32 and, in some instances, may be utilized in a control algorithm by the DSP to calculate the output of the generator 8 in a real time scenario.

As can be appreciated, the Vrms is, however, not measured with an external device, e.g., an RMS meter 56, in a real time scenario. As noted above, the gain of the log amp 46 (and/or log amp 48) is not constant across the dynamic range, see FIG. 6 for example under the V1 Gain column. The gain value changes from 132 to 140 in a non-linear relation. This gain variation is prevalent for both log amps 46 and 48. Therefore, in a surgical environment, the DSP 28 utilizes one or more control algorithms to calculate the gain to calibrate the sensor 38 and/or sensor 40. The DSP 28 uses the above data to fully automate the calibration of the sensor 38 (and/or sensor 40) by calculating the slope of the log amp 46 (and/or log amp 48) utilizing one or more of the aforementioned equations. The overall gain of the measurement module 21 is subsequently calculated and utilized by the DSP 28 to accurately calculate the Vrms, impedance and/or the power at the tissue site.

In particular, and in one embodiment, the calibration computer system 16 utilizes a control algorithm that incorporates a piece-wise linear fit of the gain relative to the measured output of the log amp 46 to correct the variations in gain of the log amp 46. In this instance, for example, the data of table (1) may be stored into memory 22 and accessed by the DSP 28. When the output of the voltage log amp 46 detected by the DSP 28 falls between two known values the gain is calculated using a linear slope equation:

$$\text{Gain\_Calc} = mX + b \quad (11)$$

in this equation Gain_Calc is the calculated gain value, X is the V1raw data from table (1), m is the slope between the two known gain points, and b is a calculated offset. It should be noted that the "Gain_Calc" in equation (11) is not the same as the "Gain" in equation (10). Gain_Calc" is the gain between two gain values (e.g., 134.96 and 140.27) previously calculated and stored into memory 22. For example, if the detected output from the log amp 46 is 2.10, which falls between an output of log amp 46 that equals 1.96 (see table (1) in FIG. 5) and an output of the log amp 46 that equals 2.24 (see table (1) in FIG. 5) the DSP 28 utilizes equation (11) below and the corresponding gains to calculate the Gain_Calc.

$$m = (\text{Gain2} - \text{Gain1})/(\text{Log\_out2} - \text{Log\_out1}) \quad (11)$$

To calculate m, Gain 1 is a first gain point (134.96), which corresponds to an output of the log amp 46 that equals 1.96 and Gain 2 is a second gain point (140.27), which corresponds to an output of the log amp 46 that equals 2.24 (see FIG. 6).

Log_out1 is the output of the voltage log amp 46 in relation to the first gain point (1.96) and Log_out2 is the output of the voltage log amp 46 in relation to the second gain point (2.24), see FIG. 6. In this example, m is equal to 18.96.

$$b=\text{Gain1}-m*(\text{Log\_out1}) \quad (12)$$

Continuing with the present example, and using equation (12) above, b is calculated to be equal to 97.8.

Taking the values found for b and m and using them in equation (11), the corresponding output of the log amp 46 is equal to 2.10 and the gain is found to be equal to 137.62.

The DSP 28 utilizes this gain value of 137.62 in equation (10) to accurately calculate Vrms, impedance and/or the power at the tissue site. The slope is assumed to equal 39 mV. The calculated value of the gain (137.62) is substituted into equation (10), Vrms is calculated to be $(137.62)10^{[(2.10-2.95)/(20\times0.039)]}$, which is equal to Vrms=$(137.62)10^{(-0.85/0.78)}$, which is equal to Vrms=$(137.62)10^{(-1.089)}$, which is equal to Vrms=11.192. This value of Vrms falls between the previously measured Vrms values 17.1 and 7.3 that correspond to the outputs 2.24 and 1.96 of the log amp 46.

In some embodiments, the calibration computer system 16 utilizes a control algorithm that incorporates an averaging technique of the gain relative to the measured output of the log amp 46 to correct the variations in gain of the log amp 46. In this instance, the log amp 46 gain values from the individual calibration points across the dynamic range are averaged together to get a mean gain for the error over the dynamic range of the voltage log amp 46. In this instance, the DSP 28 calculates the mean gain value over the dynamic range and substitutes this gain in equation (10) and then calculates the Vrms (or other desired parameter at the tissue site).

In some embodiments, the calibration computer system 16 utilizes a control algorithm that incorporates a polynomial curve fitting technique ("poly-fit" technique) of the gain relative to the measured output of the log amp 46 to correct the variations in gain of the log amp 46. In this instance, one or more suitable polynomials may be utilized to represent the gain variations of the voltage log amp 46. For example, a typical third order polynomial:

$$V=a*V\text{calc}^3+b*V\text{calc}^2+c*V\text{calc}+d$$

where a, b, c, and d are the polynomial calibration coefficients may be utilized to represent the gain variations of the voltage log amp 46.

Operation of the electrosurgical system 2 is described with reference to the piece-wise linear fit algorithm. In this instance, it is assumed that the data of table (1) has been previously calculated for the log amp 46 and stored into memory 32 of the main processor 30.

In use, the DSP 28 receives an output, e.g., an output voltage, from the log amp 46. DSP 28 runs through the piece-wise linear fit control algorithm to calculate a gain of the log amp 46. Thereafter, the Vrms is calculated utilizing the calculated gain in equation (10). Once the Vrms is calculated, the DSP 28 can communicate control signals as needed to ensure that the generator 8 provides a correct amount of electrosurgical energy to the forceps 4.

The electrosurgical system 2 including the generator 8 and calibration computer system 16 provides an effective method of calibrating the sensors 38 and 40 to overcome the aforementioned drawbacks that are typically associated with conventional generators.

From the foregoing and with reference to the various figure drawings, those skilled in the art will appreciate that certain modifications can also be made to the present disclosure without departing from the scope of the same. For example, various temperature ranges could utilize their own multi-point calibrations to compensate for any temperature dependency of the log amp 46 and/or log amp 48.

Moreover, it is within the purview of the instant disclosure to utilize a plurality of log amps 46 and a plurality of log amps 48. As can be appreciated, this adds an extra layer of sensing capabilities, which, in turn may increase overall gain of the measurement module 21.

Further, the aforementioned control algorithms may utilized in combination with one another. For example, the DSP 28 may utilize a piece-wise linear control algorithm across a first portion of the dynamic range of the log amps 46 and 48 and may utilize the averaging (or poly-fit) control algorithm across a second, different portion of the dynamic range of the log amps 46 and 48.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system for performing an electrosurgical procedure, comprising:
an electrosurgical generator including at least one microprocessor and a measurement module including at least one log amp in operative communication with the processor; and
a calibration computer system operably coupled to a measurement device configured to measure parameters of an output signal generated by the electrosurgical generator, the calibration computer system configured to compile the measured parameters into at least one data look-up table and couple to the electrosurgical generator for transferring the at least one data look-up table to memory of the electrosurgical generator,
wherein the microprocessor is configured to receive an output from the at least one log amp and access the at least one data look-up table from memory to execute at least one control algorithm for controlling an output of the electrosurgical generator, the at least one control algorithm including:
calculating a slope and gain of the log amp; and
correcting gain variations of the log amp based on a piece-wise linear fit of the gain relative to the measured output of the log amp.

2. The electrosurgical system according to claim 1, wherein the at least one log amp is configured to receive an output from a sensor that is configured to sense an output of the electrosurgical generator.

3. The electrosurgical system according to claim 1, wherein the measurement device is an RMS current device.

4. The electrosurgical system according to claim 1, wherein the measurement device includes a current toroid that is configured to measure an output current of the electrosurgical device.

5. The electrosurgical system according to claim 1, wherein the output from the at least one log amp is a voltage output.

6. The electrosurgical system according to claim 1, wherein the parameters contained in the data look-up table include at least one of gain of the at least one log amp, output voltage of the at least one log amp, input voltage of the at least one log amp, output current of the electrosurgical generator and output voltage of the electrosurgical generator.

7. The electrosurgical system according to claim 1, wherein the slope and gain of the log amp are calculated through a dynamic operating range of the log amp.

8. The electrosurgical system according to claim 7, wherein the log amp is configured to allow a user to vary a slope thereof to obtain an optimum slope through the dynamic operating range.

9. The electrosurgical system according to claim 7, wherein both the voltage and current sensors are isolated from a patient and referenced to ground of the electrosurgical generator by at least one of isolating and reducing a voltage sense line with the use of a plurality of capacitors.

10. The electrosurgical system according to claim 1, wherein the control algorithm utilizes an averaging technique of the gain relative to the measured output of the log amp to correct gain variations of the log amp.

11. The electrosurgical system according to claim 1, wherein the control algorithm utilizes a polynomial curve fitting technique of the gain relative to the measured output of the voltage log amp to correct the variations in gain.

12. The electrosurgical system according to claim 1, wherein the measurement module includes a voltage and a current sensor that are configured to measure voltage and current, respectively, on a patient side of an output transformer of the measurement module.

\* \* \* \* \*